(12) United States Patent
Troyk et al.

(10) Patent No.: US 7,271,677 B2
(45) Date of Patent: Sep. 18, 2007

(54) INDUCTIVE DATA AND POWER LINK SUITABLE FOR INTEGRATION

(76) Inventors: Philip Richard Troyk, 6027 Capulina Ave., Morton Grove, IL (US) 60053; Glenn Anthony DeMichele, 90 Elmwood Ln, Lincolnshire, IL (US) 60069

( * ) Notice: Subject to any disclaimer, the term of this patent is extended or adjusted under 35 U.S.C. 154(b) by 581 days.

(21) Appl. No.: 10/664,363

(22) Filed: Sep. 22, 2003

(65) Prior Publication Data

US 2005/0063488 A1    Mar. 24, 2005

(51) Int. Cl.
*H03C 3/00* (2006.01)
(52) U.S. Cl. .................. 332/100; 329/300; 340/506; 340/825.58; 340/572.5
(58) Field of Classification Search ............ 332/100; 329/300; 340/506, 825.54, 572, 825.58, 340/527.5
See application file for complete search history.

(56) References Cited

U.S. PATENT DOCUMENTS

| 4,517,519 | A | | 5/1985 | Mukaiyama |
| 4,681,111 | A | | 7/1987 | Silvian |
| 5,559,507 | A | * | 9/1996 | Beigel ............... 340/10.34 |
| 5,999,857 | A | | 12/1999 | Weijand |
| 6,201,993 | B1 | | 3/2001 | Kruse |
| 6,943,680 | B2 | * | 9/2005 | Ward, Jr. ............... 340/506 |

* cited by examiner

*Primary Examiner*—Arnold Kinkead
(74) *Attorney, Agent, or Firm*—Don W. Weber (57) ABSTRACT

A system providing an inductive power and data link between an external transmitter and miniature internal receiver is presented. The system is suited to applications where the receiver must be of a small size and the system must consume very little power, such as an implanted biomedical device. The system is also compatible with systems where bi-directional communications are required. The novel transmitter and receiver form an improved forward data telemetry system. The transmitter consists of a Class-E converter with its optimum operating frequency being synchronously, instantaneously and efficiently altered in accordance with the data to be transmitted, thereby producing an FSK modulated magnetic field of substantially constant amplitude. The constant amplitude output allows for the continuous, data-independent transfer of power to the miniature receiver and its associated electronics. The present invention also represents an improvement over the high efficiency Class-E converters previously patented by the inventors. The receiver consists of a coil and an integrated rectifying system to recover operating power from the incident magnetic field, as well as an FSK demodulator whose operation is based on the multiphase comparison of charging times of integrated capacitors. The described FSK demodulator approach removes deleterious effects resulting from low-frequency changes in the transmitter frequency, and eliminates time distortion artifacts generated by circuit imbalances and asymmetries in the power recovery process. The combination of the transmitter and receiver improvements yields a reliable data transfer system unaffected by circuit imbalances and incidental variations in the amplitude and frequency of the magnetic field.

7 Claims, 10 Drawing Sheets

INDUCTIVE DATA AND POWER LINK SUITABLE FOR INTEGRATION

BACKGROUND OF THE INVENTION

This invention relates to inductively coupled data links. More particularly, the invention establishes combined power transfer and reliable "forward telemetry" data communications between an external transmitter and an internal miniature low power receiver such as might be found in an electronic medical implant, The invention described herein was developed to communicate with an implantable medical device, but may also be effectively applied to other applications, such as some RFID transponders, for which data must be sent from an external transmitter to internal device electronics. In all of these devices miniaturization is important. Therefore, optimizing the combination of power and communication transfer from a transmitter to implant or miniature internal device while maintaining small size is crucial. To accomplish this an efficient means of remotely powering and providing telemetry data to the implant, as well as a robust means of demodulating the telemetered data within the implant are needed. A novel transmitter embodiment, and a novel receiver embodiment is described. The transmitter and receiver, in combination, yield an improved forward data telemetry system.

Short-range electronic communication using magnetic coupling is presently used in many diverse applications. These applications include implantable medical electronics, radio frequency identification systems, wireless control of actuators, and sensor-to-indicator communications.

In a typical magnetically-coupled system, an external transmitter generates a relatively strong AC magnetic field by driving radiofrequency (RF) current into a transmitter coil. The external transmitter is typically comprised of a High-Q resonant circuit, commonly known in the art to be made up of low-loss RLC components, having a Q greater than about twenty. The transmitter modulates this field, in accordance with an incoming stream of data, by changing the nature of the transmitter coil current. An internal coil, connected to the internal receiver, changes the magnetic field into a current. The internal receiver detects data modulation on this current and extracts the data, which then may be used by other functional elements in the internal assembly. The magnetic field may also be used to power the internal electronics, thereby removing the requirement for a battery in the internal electronics. The combination of the external transmitter coil and the internal coil, contained within the internal device, is called a magnetic link. A device powered solely by the external magnetic field, through the magnetic link, is termed "passive".

Various electrostatic and electromagnetic transponders (described in US Patents issued to Vega et al. U.S. Pat. No. 6,147,605, Carrender et al. U.S. Pat. No. 6,107,917, O'Toole et al U.S. Pat. No. 6,130,602 and U.S. Pat. No. 6,157,230) are described for use as RFID tags. These transponders typically operate in the medium to high frequency range (8 MHz-1 GHz) and can have long range and demonstrate high data bandwidths. Magnetically coupled systems typically operate at lower frequencies (10 kHz-10 MHz) and typically demonstrate shorter range and lower data bandwidths. A magnetically coupled system however is minimally affected by immersion in a conductive medium and orientation of the receiver coil in the exciting magnetic field. Magnetic coupling also enables the use of passive transponders. These are required features for an implantable transponder. The invention described herein is a magnetically coupled data and power transmission system, with modulation and demodulation techniques developed and applied in a manner to optimize the performance of the system. To fully understand and appreciate the improvements of the instant invention, the prior art must be explored while considering the system-level objectives of the invention.

For optimal system performance, a transmitter in this type of application must generate a strong magnetic field as efficiently as possible. Low power conversion efficiency results in weaker magnetic fields, the unnecessary generation of heat, and shorter battery life, for portable applications. In order to have a reasonable separation between the transmitter and the internal device, large currents must exist in the transmitter coil, and transmitter coil quality factor (Q) is the first and necessary limitation of transmitter power efficiency. Often, a resonant capacitor is used with the inductance of the transmitter coil, and the non-infinite Q of this capacitor further degrades the efficiency of the transmitter. Transmitter embodiments exist using topologies that require that a substantial portion of the transmitter coil current pass through semiconductor switching elements (see, for example the US patents issued to Silvian U.S. Pat. No. 4,681,111, Biegel U.S. Pat. No. 5,559,507, Weijand et al. U.S. Pat. No. 5,999,857, Crosby et al. U.S. Pat. No. 4,532,930, and Milheiser U.S. Pat. No. 5,166,676). However, in these applications, the semiconductor losses are usually larger than the Q losses of the resonant elements, and substantially degrade the system's power efficiency.

In order to communicate with the internal device over the magnetic link, the current in the transmitter coil must be modulated. The transmitter modulation method must have a minimal impact on transmitter power efficiency, and must be readily implemented with available components. If powering of the internal device is required, the modulation method should not result in the disappearance of the powering magnetic field for a significant period of time, since that would interrupt power to the internal electronics. The instant invention uses frequency-shift-keyed (FSK) modulation to transfer data from the transmitter to the receiver while maintaining a magnetic field of near constant amplitude in order to supply continuous receiver power.

Weijand et al, '857. describe an FSK transmitter topology where the resonant frequency of a series-resonant circuit is selectively altered by using a MOSFET switch to place a capacitor directly across the antenna coil. In addition to the previously mentioned losses resulting from series switching of the transmitter coil current, this topology is limited in its application to low transmitter power. To achieve coil currents of several Amperes in the 100 kHz, or above, frequency range, it is not unusual to observe transmitter coil voltages approaching 1000 Volts. The MOSFET switching element as used by Weijand must withstand this voltage, necessitating the use of a high-voltage power MOSFET. To maintain acceptable power efficiency when the MOSFET is conducting, the "On" resistance of the MOSFET device must be as low as possible, necessitating a physically large MOSFET device. Such a device will demonstrate large parasitic drain and gate capacitances. The large gate capacitance degrades power efficiency because of the large drive currents required to initiate MOSFET switching. The large drain capacitance appears in parallel with the transmitter coil when the MOSFET is off, thereby lowering the resonant frequency of the network when the cited FSK system is in the high-frequency state. This drain capacitance will therefore limit the frequency of operation of the system. In practice implementing the techniques described in the '857 patent requires the use of a high-voltage, low-on resistance, low-capacitance MOSFET, and such MOSFET devices are not presently available. It is an object of this invention to use a transmitter topology that enables the use of a low-voltage MOSFET, low-on-resistance MOSFET, high-capacitance MOSFET, to alter the operating frequency of a high-power, High-Q resonant transmitter circuit.

Griffith, U.S. Pat. No. 6,073,050, describes a low-power Class-E transmitter as one type of the High-Q resonant circuit transmitter, operating at 49 MHz The '050 patent describes amplitude modulation of the transmitter to provide adjustable power to an implanted device, with no provision for FSK modulation of the Class-E converter. The operation of a Class-E converter was also described in prior art by Co-inventor Troyk (et al.) in U.S. Pat. No. 5,179,511 Self-regulating Class E Resonant Power Converter Maintaining Operation in a Minimal Loss Region. It is another object of this invention to offer a novel way to frequency modulate the converter previously described by Troyk, et al.

For the receiver circuitry contained within the internal (implanted) miniature device, in an application such as the one herein, the demodulation method chosen must provide a reliable data link, which also should not be compromised by variations in magnetic field strength. Such variations are typically due to movement of the internal electronics, or magnetic link, with respect to the external transmitter, movement of nearby metallic objects, or variations in the external transmitter power supply. In addition to these conditions, variations in power consumption of the implanted electronics will vary the nature of the current in the implanted coil. The data demodulation process must be immune to these variations or data errors may occur. Since the receiver is often to be implanted, or embedded, complete integration of the receiver electronics is required primarily for miniaturization, and secondarily for power minimization.

Several references related to data telemetry describe in detail conventional FSK demodulation techniques as a component of a proposed system (Kruse et al. U.S. Pat. No. 6,201,993, Hogrefe et al. U.S. Pat. No. 4,561,443). Others simply state that their embodiments may employ FSK or FM techniques to realize data transfer without offering specifics on how the FSK demodulation is to be performed (see, for example, Silvian U.S. Pat. No. 4,681,111, Urbas et al. U.S. Pat. No. 5,532,686, Juengel U.S. Pat. No. 4,742,470). In the '111 patent, the problem of response time for FSK demodulation is described. Traditionally, FSK demodulators suffer from the problem of slow response due to the need for either a phase-locked-loop, or other time-constant driven circuit to respond to changes in the FSK modulation. The slow response time limits the data rate of the system relative to the transmitter frequency.

Prior art also describes an FSK demodulator suitable for integration (Mukiayama U.S. Pat. No. 4,517,519) that compares zero crossing times of an input signal of unknown frequency with a known internal reference frequency. The '519 invention is significant in that it teaches a system that can be fully integrated on a single silicon substrate, an important requirement for miniaturized implantable devices. This technique is not applicable in certain important applications, because for these the implanted receiver has only the transmitter magnetic field as its clock, and no reference frequency is available. Therefore the '519 techniques cannot be used. It is a still further object of this invention to provide a transmitter/receiver system that overcomes these obstacles related to the availability of reference frequencies.

Mimura et al. U.S. Pat. No. 5,309,113, describe the use of a fixed delay and mixers to discern the input frequency. Hendrickson et al. U.S. Pat. No. 5,933,455, describe an FSK data slicer using the charging time of a capacitor as a time reference and over-sampling of the results to improve data reliability. It is a still further object of this invention to disclose a new approach to the problem that the unavailability of a time reference and over-sampling procedures require.

The invention described herein uses the charging time of multiple capacitors in a multi-phase fashion as a time reference. This eliminates the need for over-sampling and the need for a higher frequency clock. This is a particularly salutary feature since a frequency clock is not typically available in a miniaturized electronics application such as the one presented here.

The prior art does not disclose an FSK demodulation technique that automatically accommodates for asymmetries in the incoming waveform's detected period due to rectification artifacts. These rectification artifacts are characteristic of all transponder or medical implant implementations where power and data are transferred over a magnetic link simultaneously via a magnetic field. It is a still further object of this invention to addresses a significant need for a transmitter/receiver system that can operate without the need for a fixed time clock or over-sampling of data.

SUMMARY OF THE INVENTION

The invention consists of an improved power and telemetry system. Both the transmitter and receiver are improvements over the prior art. The transmitter improvement includes a practical low-loss method of instantaneously shifting the operating frequency of a High-Q resonant circuit transmitter, such as a Class-E converter, thereby allowing the efficient generation of an FSK modulated high power magnetic field.

The receiver improvements consist of a novel multiphase FSK demodulator, and decoding logic to accurately decode the transmitted data bit stream. The FSK demodulator measures the time between zero crossings of an input signal proportional to the instantaneous cyclic variation of the FSK modulated magnetic field. By comparing these detected periods to the average period of the incoming signal an adaptive threshold is realized, thereby producing a demodulator that is insensitive to any low-rate drift in the frequency of the magnetic field. Furthermore, by maintaining different averages for the positive and negative half-cycles of the incoming signal, the FSK demodulator is rendered insensitive to any inequality of the positive and negative pulse widths. Such asymmetry typically occurs in magnetic-link powered devices due to an imbalance in stray capacitance at the receiver coil, or because of synchronous variations in the load current supplied to the rest of the receiver electronics by the receiver's rectification system.

The FSK decoding logic combines the results of the positive and negative phase comparisons to produce a decoded bit stream. In order for the adaptive threshold to be maintained midway between the transmitter's high and low frequency operating points, the data encoding method used must result in the long term equality of high and low frequency transmitter cycles.

BRIEF DESCRIPTION OF THE DRAWINGS

For a better understanding of the Specification below, reference is made to the accompanying drawings, in which:

FIG. 2E' shows the contents of the identical hierarchical blocks 105-108. The port names on FIG. 2E' correspond with the pin names on the blocks in FIG. 2E.

FIGS. 3C1, 3C2 and 3C3 show the schematic of the bit decoding logic in integrated form. FIGS. 3C1, 3C2 and 3C3 are interconnected by the port connectors which connect ports of identical names, for example ACK is connected to all other connectors named ACK.

DETAILED DESCRIPTION OF THE PREFERRED EMBODIMENT

Figure 1A:
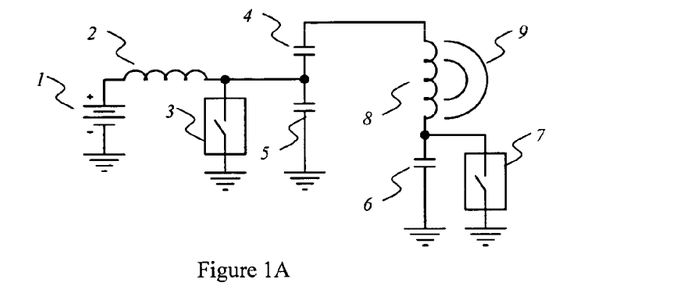
FIG. 1A shows the topology of the Class-E converter described by Troyk et al. with the addition of frequency shift keyed capability.

Detailed operation of an unmodulated Class-E converter used in a transmitter circuit may be further understood by referring to a United States patent issued to co-inventor Troyk (et al.), U.S. Pat. No. 5,179,511 entitled Self-regulating Class E Resonant Power Converter Maintaining Operation in a Minimal Loss Region. Referring to FIG. 1A herein, the standard Class-E converter consists of a resonant circuit comprised of inductor 8 (a coil), and capacitors 4 and 5. The frequency of operation is determined roughly by the value of inductor 8 and the value of capacitor 4 in series with capacitor 5. The resonant current in inductor 8 produces a magnetic field 9 that powers the implanted receiver electronics. MOSFET switch 3 is pulsed in synchrony with the resonant coil current by external control circuitry (not shown), thereby transferring energy from inductor 2 into the resonant circuit when the voltage at MOSFET switch 3 is substantially zero volts. This mode of operation results in large currents in only the resonant elements, thereby greatly reducing power losses in the MOSFET switch. It is important to note that the voltage at inductor 8 may be very high in high-power transmitters. The fact that capacitor 5 is chosen to be substantially larger than capacitor 4 results in a beneficial capacitive voltage division, thereby reducing the voltage stresses on MOSFET switch 3.

The addition of capacitor 6 and MOSFET switch 7 to the prior art converter enables the operating frequency of the converter to be efficiently and instantaneously raised and lowered. This allows for more than one distinct states of frequency to be defined. Switching between these distinct frequency states can be accomplished substantially instantaneously with an approximately zero transition time, 1-5 degrees of a cycle, by electronic switching of stored energy within the circuit. Storage of the energy used for creating the distinct frequency states used for FSK modulation can be accomplished using either capacitors or inductors as is commonly known to those skilled in the art. With this understanding of the basic operation of the invention, a more explicit description of its operation follows:

MOSFET switch 7 is characterized by conducting (low on-resistance) and non-conducting (high off-resistance) states, as is well-known in the art, and is turned on (to the conducting state) when the voltage across it is substantially zero volts by external control circuitry (not shown). Since the initial voltage on capacitor 6 is zero volts, no energy is transferred, or lost, when MOSFET 7 is turned on. When MOSFET 7 is turned on, capacitor 6 has no effect upon the resonant frequency of the converter. MOSFET 7 can be switched off (to the non-conducting state) with no associated energy loss when the current through inductor 8 is at a zero-crossing. Under this condition, capacitor 6 has been placed in series with capacitor 4 and has thus altered the resonant frequency of the converter. Even when operating in the 10 MHz range, capacitors 5 and 6 are much larger in value than the typical parasitic low-voltage MOSFET drain capacitances. Therefore the characteristics of MOSFET 7 can be chosen so as to minimize its on resistance. To return to the higher-frequency state of operation, MOSFET switch 7 is turned off when the current through it is substantially zero amperes. The converter is therefore ready to lower its operating frequency yet again upon command. Using these new techniques, the modulation of the transmitter can occur with little to no, on the order of 1% or less, energy loss.

Figure 1B:
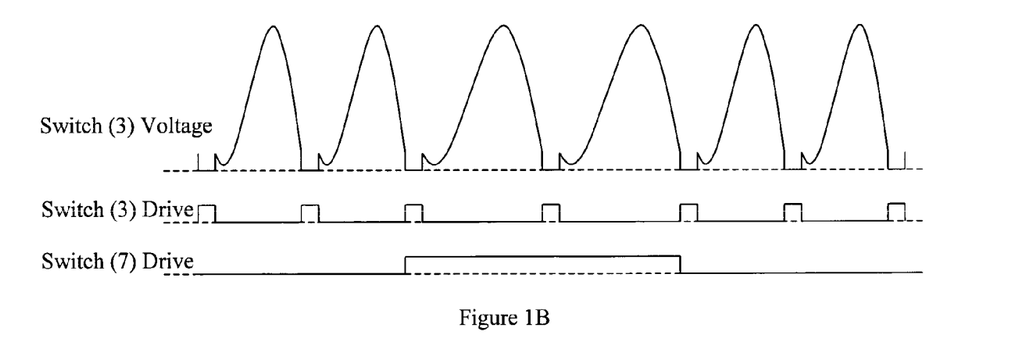
FIG. 1B shows representative waveforms of the modified Class-E converter in operation.

Referring to FIG. 1B, the voltage at MOSFET switch 3 is shown along with the drive signals to MOSFET switches 3 and 7. Using this low-loss method to FSK modulate a Class-E converter yields the ability to transfer data to an implanted receiver, yet keeps the amplitude of the magnetic field that powers the receiver electronics substantially constant. Although the preferred embodiment is described for a Class-E converter, the same techniques can be applied to a broad range of resonant circuit transmitter topologies, as are well known to those skilled in the art.

Figure 2A:
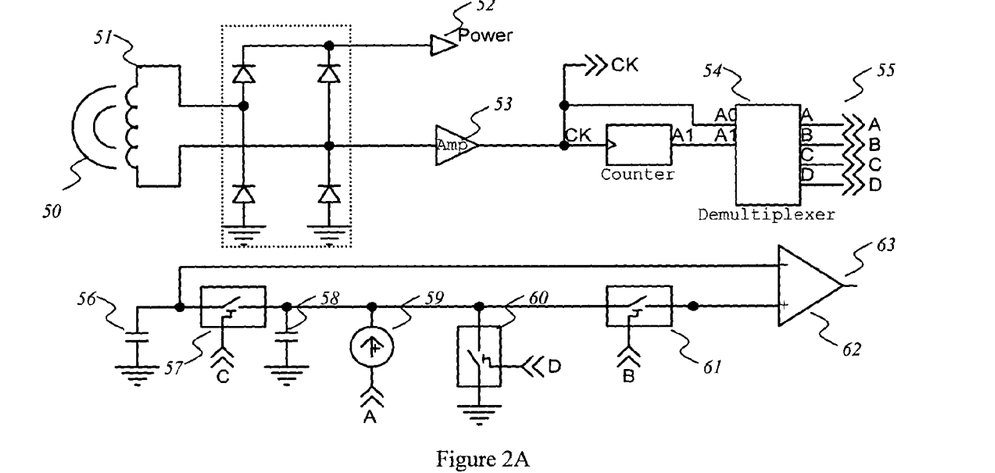
FIG. 2A shows a single-phase embodiment of the FSK detector, and is used as a basis for understanding the multi-phase preferred embodiment.
Figure 2B:
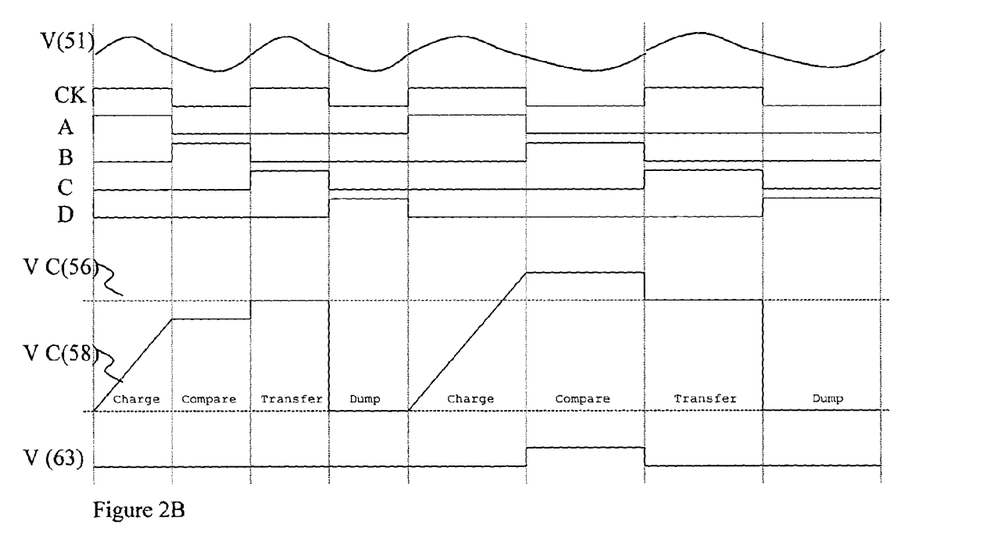
FIG. 2B shows representative waveforms associated with the single-phase FSK detector.

The FSK demodulator in the receiver consists of a multi-phase demodulator, used as an FSK detector, and logic to assess the results of the detection process, thereby providing a fully demodulated data bit stream and data clock. To understand the operation of the multi-phase FSK detection, a single-phase detector and its representative waveforms are shown in FIGS. 2A and 2B respectively. The single-phase detector is certainly a useful invention, but a multi-phase detector improves system performance by effectively increasing the signal sampling rate as well as allowing the rejection of rectification artifacts present in magnetically powered receiver systems. In the following description, the receiver has been stimulated by two cycles at the high transmitter frequency, followed by two cycles at the low transmitter frequency.

The magnetic field 50 from the transmitter induces current in receiver coil 51. A diode bridge to provide DC power 52 to the rest of the receiver system rectifies this current. The voltage at 51 is shown in the first trace of FIG. 2B. Amplifier 53 amplifies the incoming voltage to produce a square-wave clock "CK", shown as the second trace of FIG. 2B. The CK signal is divided by two, and this signal and CK are used to drive a demultiplexer 54 which produces outputs 55 termed A, B, C, and D. These outputs can be seen in traces 3 through 6 of FIG. 2B to be simple "one-of-four" outputs used to define four states. In the single-phase example, these states may be described as "Charge", "Compare", "Transfer", and "Dump".

In the Charge state, capacitor 58 is charged from zero volts by constant current source 59. The voltage on capacitor 58 is shown in trace 7 of FIG. 2B. The voltage present on capacitor 58 at the end of the Charge state depends on the charging current, the capacitor value, and most importantly the time duration of the Charge state. At the end of the Charge state, current source 59 is turned off, and switch 61 is closed, so comparator 62 is called on to compare the final voltage on capacitor 58 to a reference voltage on averaging capacitor 56. This reference voltage is also shown as a constant value on trace 7 of FIG. 2B as a dotted line. The output of the comparator 63 is shown in trace 8 of FIG. 2B, and it can be seen that the comparator 63 output state depends upon whether or not the Charge state lasted long enough to allow the voltage on capacitor 58 to exceed the reference. This is how FSK is detected. The reference voltage on averaging capacitor 56 is the frequency detection threshold. As will be seen, the proper derivation of this reference voltage is critical to the operation of the invention.

After the Compare state, the Transfer state is entered, where only switch 57 is closed, transferring the charge on capacitor 58 onto the much larger averaging capacitor 56. This charge transfer occurs regardless of the final value achieved on capacitor 58 during the Charge state, so the voltage accumulated on averaging capacitor 56 is the average of more than one final voltages present on capacitor 58 at the end of recent Charge states. The length of this running average is dependent on the ratio of the values of capacitor 56 and capacitor 58, and is typically selected to produce an average over a range of 10 to 100 bit periods. If an FSK data modulation method is chosen which maintains equal numbers of high and low frequency transmitter cycles over the averaging time, the reference voltage on reference capacitor 56 will provide a slicing threshold midway between the final voltage states of capacitor 58 for low and high frequency detection events. Thus the operation of this circuit is that of an adaptive threshold detector. Operating frequency drift of the transmitter due to thermal or component variation, or even the movement of metal objects within the magnetic field, typically occur much more slowly than the averaging time of the reference capacitor 56. In this way, an adaptive midscale slicing threshold is maintained in the presence of transmitter frequency drift.

Figure 2C:
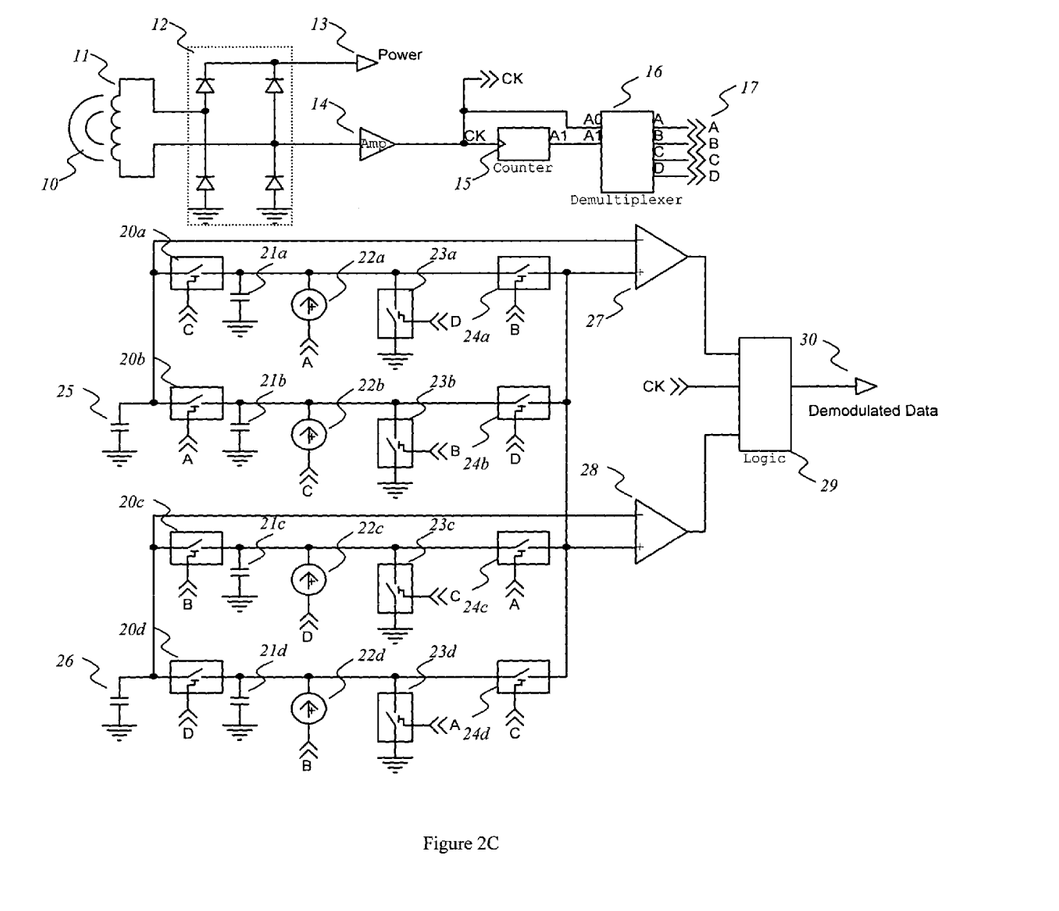
FIG. 2C shows the multi-phase preferred embodiment of the FSK detector.
Figure 2D:
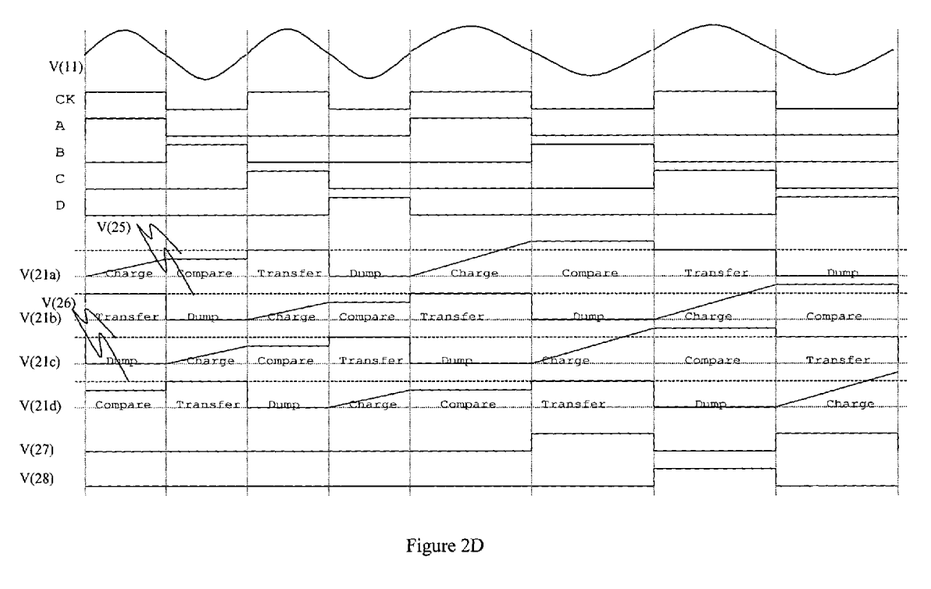
FIG. 2D shows representative waveforms associated with the multi-phase FSK detector.

FIGS. 2C and 2D show the block diagram and associated waveforms respectively for the multi-phase FSK detector. The magnetic field 10 from the transmitter produces a receiver coil 11 voltage in a manner identical to the previous example. The Amplifier 14 produces, via demultiplexer 16, the outputs 17 A, B, C and D as before. These waveforms are shown in the first six traces of FIG. 2D. In the multiphase implementation, the single-phase detector circuit is duplicated four times, with each instance of the single-phase detector having its own charging capacitor, C21 (a, b, c, d). The voltage across each of these four charging capacitors during operation is shown in traces 7, 8, 9 and 10 of FIG. 2D. By staggering the phase of the A, B, C, D control signals to the single-phase instances, the instances collectively accomplish a Charge, Compare, Transfer and Dump operation on every single half cycle of the input waveform. This produces a comparison every half cycle of the input waveform, which is of course four times as many comparisons produced by the single-phase example. This increased sampling rate allows the logic to ascertain the frequency shift time of the transmitter to one-half-cycle resolution.

Another important feature of the multiphase implementation is the fact that either one, or two, or more, separate averaging capacitors C25, C26 may be used. In a magnetically powered system, asymmetric stray capacitance at the coil terminals 11 is likely to cause pulse width asymmetry in the widths of the input waveform on the left and right sides of the rectifier bridge 12. This manifests itself as a duty cycle of greater or less than 50% at the CK signal output of amplifier 14. This asymmetry could also be caused by asymmetrical propagation delays in the amplifier 14, counter 15 and demultiplexer 16 circuits, as well as asymmetries in layout and switch asymmetries in the single-phase instances. Another contributor to such an asymmetry is cyclic load variation of the power 13 required by the rest of the receiver electronics. Often times these electronics contain logic synchronized to the same CK signal, thereby requiring current pulses from the power 13 connection that depend upon whether the edge of the CK signal is rising or falling. This cyclic load variation results in an upset of the current balance in the legs of the rectifier bridge 12. In view of all the possible causes, it its very likely that a significant asymmetry will exist in the CK signal. By using two, or more, reference capacitors 25 and 26, the positive half cycles (CK=high) use reference capacitor 25, and the negative half cycles (CK=low) use reference capacitor C26. In this arrangement the positive and negative half cycles maintain their own adaptive thresholds resulting in valid comparisons regardless of asymmetries in CK. Without at least two reference capacitors, all half cycle periods would be compared to a threshold derived from a combined average of the positive and negative half cycle times. In addition to this threshold error, there would also be a "bobble" on the reference voltage as the alternating final charge on the charging capacitors is transferred to the single reference capacitor. This multiphase arrangement could be extended to more than four phases if, for example, a Delta or Wye multiphase coil arrangement is used in the application.

An understanding of the block diagram shown in FIG. 2C is sufficient for anyone skilled in the art to produce a physical implementation of the multiphase FSK detector. The basic topology is well-suited to integration on a single silicon integrated circuit. It is an advantage and feature of this invention that the multiphase FSK demodulator may be implemented in fully integrated form without the need for any external components such as crystals, or timing capacitors, although the technique is equally applicable to discrete circuits and those skilled in the art could apply the invention to a variety of demodulator circuits.

Figure 2E:
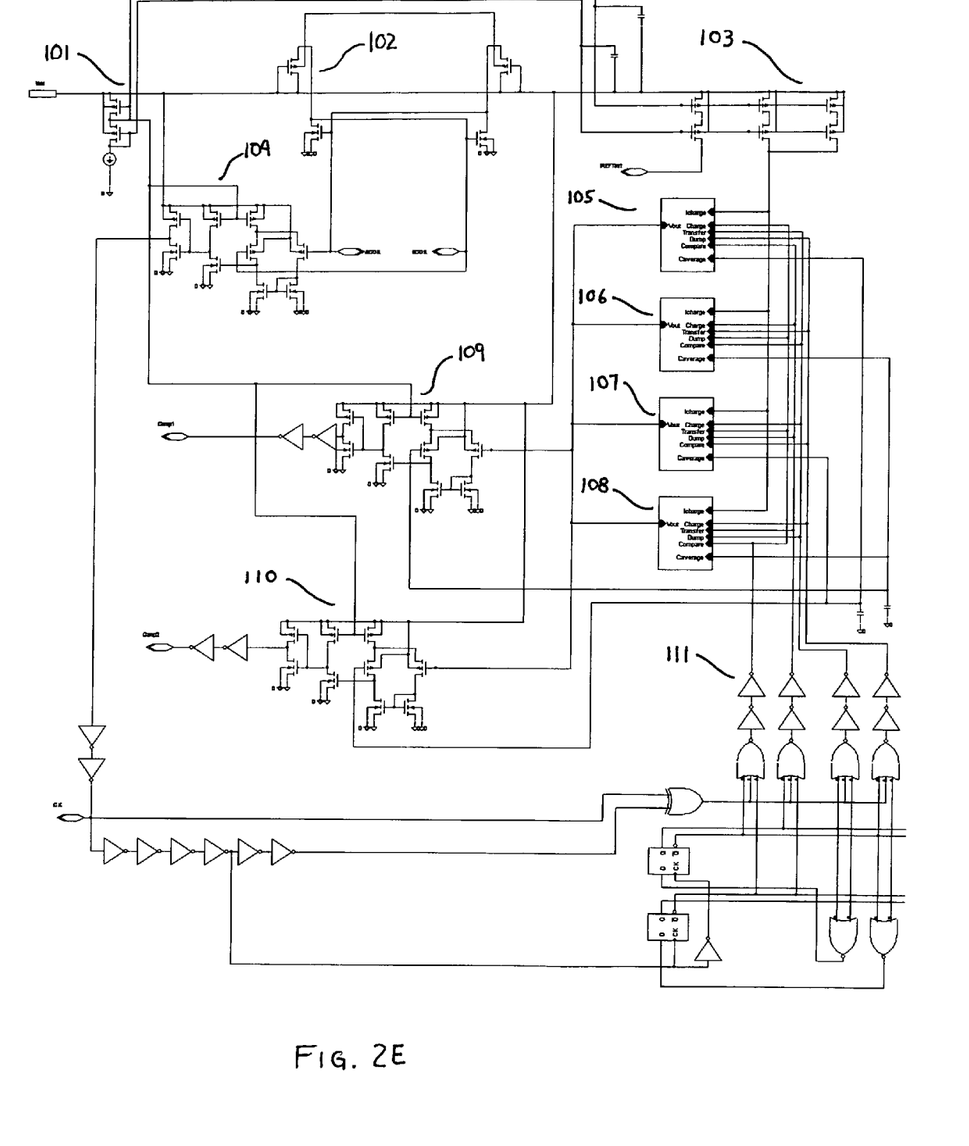
FIG. 2E shows a schematic of the multi-phase FSK detector in integrated form.

FIG. 2E shows a schematic of an integrated circuit designed to perform the multiphase FSK detection, and is included as an example of one physical embodiment. Referring to FIG. 2E, the modules are as follows:

101 Chip-wide current reference;
 102 Rectifier bridge, implement with MOSFET devices;
 103 Switched current sources to charge the capacitors in each single-phase instance;
 104 Differential amplifier used to produce the CK signal from the signal across the bridge;
 105-108 Instances of Single-phase FSK detectors;
 109, 110 Comparators that compare the charging endpoint to the reference voltages;
 111 A, B, C, D control signal generation from the CK signal.

In order to maintain a valid reference voltage on the two reference capacitors, the number of high frequency half cycles must be equal to the number of low frequency half cycles over the averaging time of the reference capacitors. In the preferred embodiment, the averaging time is on the order of 50 transmitter cycles. Alternatively, a third FSK transmitter state can be used for which the third-state transmitter frequency is set to be approximately midway between the high-frequency state and the low-frequency state during times for which no data is being transmitted. Several data protocols can satisfy the high/low frequency symmetry requirement, but the method used in the preferred embodiment will be described. There are three types of data sent in the described protocol, a data "0", a data "1" and a "Tag". A tag is a symbol pattern that does not decode legally into one of the two data states, and is used to provide frame and bit synchronization to the demodulator. The tag is also used as a "start of command" indicator to other implanted receiver electronics outside the scope of this disclosure.

Figure 3A:
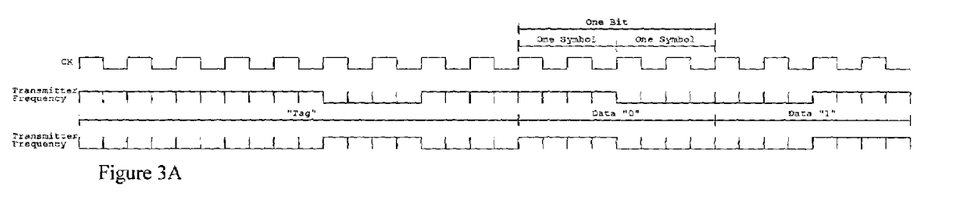
FIG. 3A shows one data encoding method compatible with the invention.

Referring to FIG. 3A, the data protocol may be simply described using the four following rules:

1) 1 Slice=½ cycle of the CK signal.
2) 1 Symbol=4 Slices.
3) 1 Bit=2 Symbols=8 Slices=4 Cycles of the transmitter signal.

The data is Manchester encoded where a data "1"=Low frequency for one symbol followed by high frequency for one symbol. Similarly a data "0" is high frequency for one symbol followed by low frequency for one symbol.

4) A Tag is 2½ Symbols or more of the same frequency (5 transmitter cycles) followed by one bit.

The bit which is part of the tag is either a data "1" or a data "0" depending upon whether the tag started with a high or a low frequency symbol. In FIG. 3A, two possibilities of tag sequences are shown, followed by a data "0", then a data "1". The FSK demodulator logic uses the transitions in the bit embedded in the tag to symbol bit and frame sync the demodulation process.

Figure 3B:
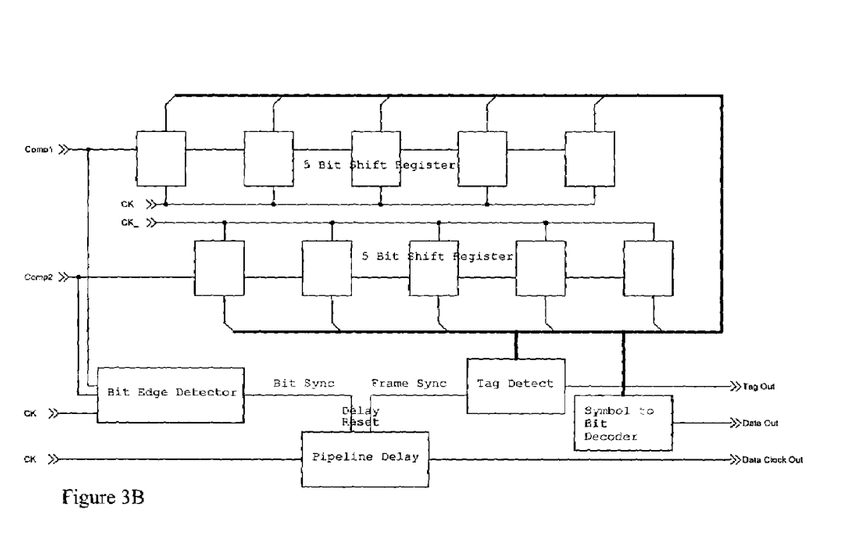
FIG. 3B is a simplified diagram of the logic method used to extract the data stream from the FSK detector.
Figure 3C:
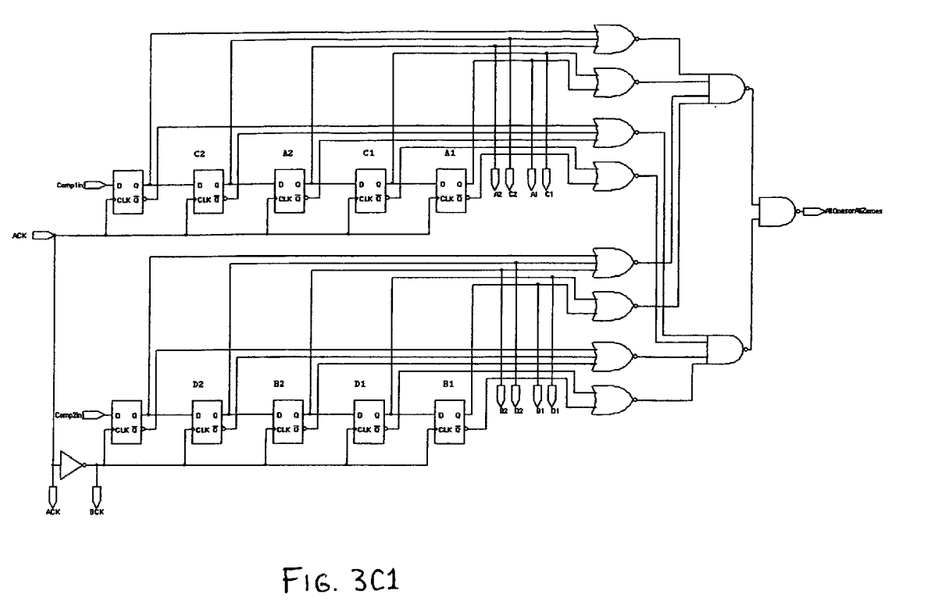
Figure 3C:
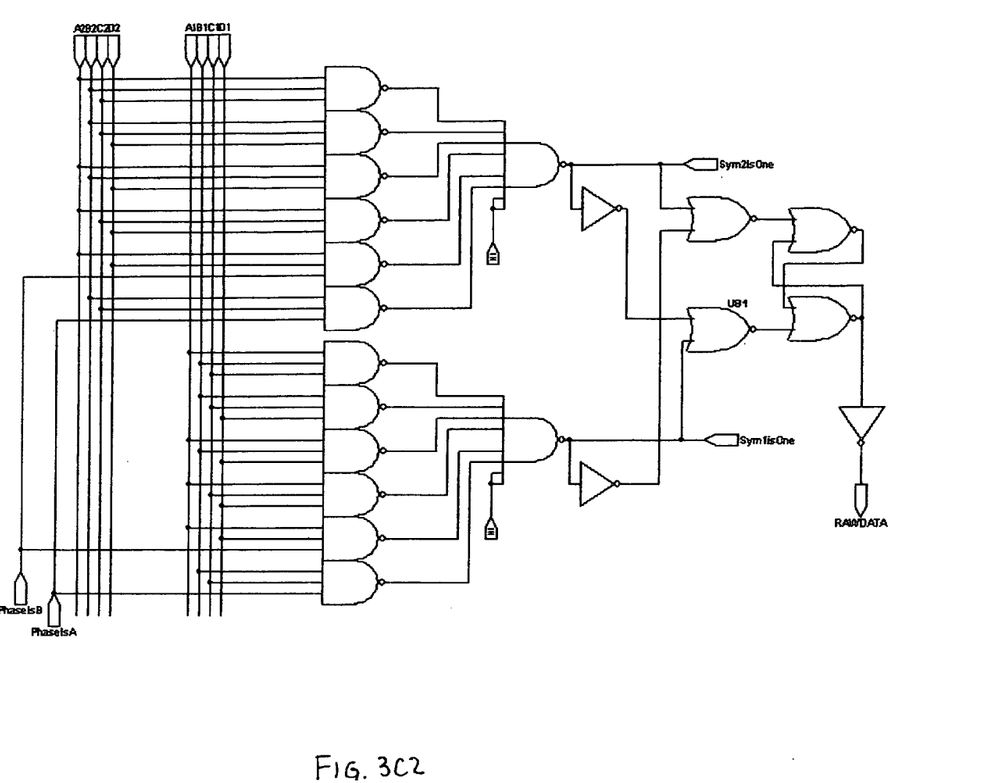
Figure 3C:
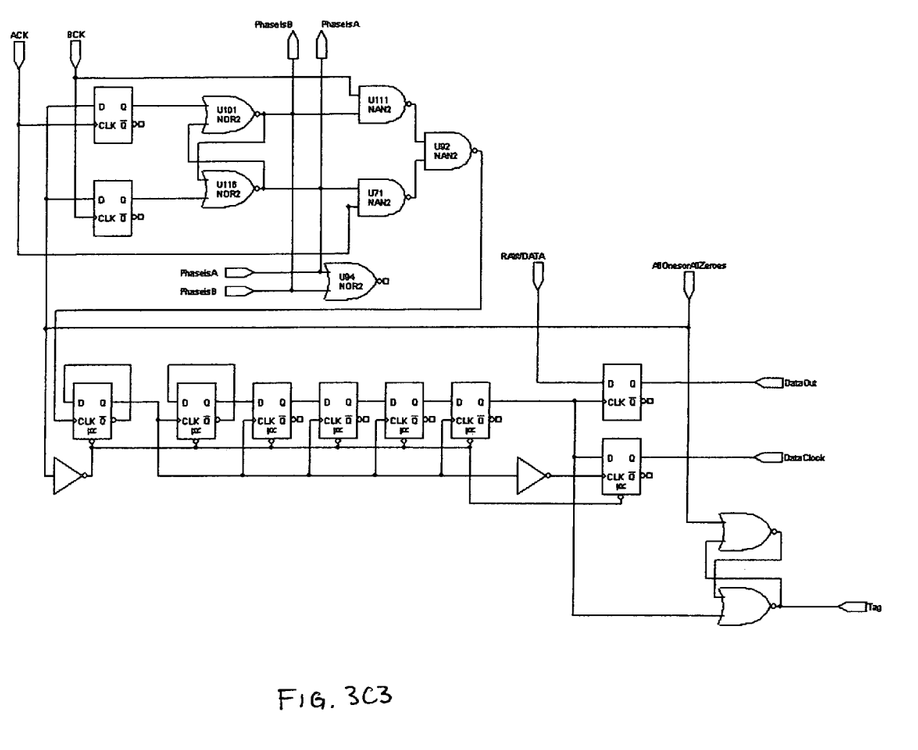

FIG. 3B shows a block diagram of the demodulation logic. Both edges of CK are used to process the incoming data, since no higher frequency clock is available within the implanted internal receiver. The two comparator outputs of the FSK detector are fed into two 5 bit shift registers, thereby maintaining a 10 Slice history of the incoming data stream. The Tag Detect logic determines when the transmitter frequency has remained at one state (high or low) for 10 Slices or more. As soon as the transmitter frequency changes to produce the embedded bit at the end of the tag sequence, the Tag Detect and Bit Edge Detector modules synchronize the Pipeline Delay to identify on which Slice the Frame, Bit and Symbol began. At the end of each bit edge after each data bit (8 Slices) is clocked into the shift registers, the Symbol-to-Bit decoder examines the 10 Slice history with combinational logic to ascertain the most probable transmitted bit existing in the register. This method allows for up to four corrupted Slices before data corruption occurs. In the event of an incorrect determination of the Pipeline Delay synchronization, the logic will resynchronize whenever no transitions exist within a bit, an illegal condition for the Manchester encoding which clearly indicates a synchronization problem. FIG. 3C is a schematic diagram of the integrated implementation of the FSK demodulator logic In the receiver, the slicing threshold used to differentiate high and low frequency half cycles of the modulated transmitter is adaptive, lies directly between the extreme values, and will track any low-rate drift in transmitter frequency. This is true for the single-phase or multiphase descriptions offered. Using a multiphase approach accomplishes two unique and novel results:

1). It allows a frequency comparison to be made on every half cycle of the transmitter.

2). Most importantly, the use of two reference capacitors compensates for any positive to negative asymmetries in the CK signal—an inevitable occurrence in these applications.

One could extend the multiphase approach to more than four phases if the application's antenna (coil) system requires. The FSK demodulator is easily implemented in an integrated circuit without using any bulky external components.

Having fully described out invention, We claim:

1. A method for frequency-shift-keyed modulation of a transmitter coil current of a high-Q resonant circuit transmitter, said transmitter having one or more distinct states of operation characterized by one or more distinct frequencies, comprising:
   storing energy within said high-Q resonant circuit transmitter; and
   switching of said stored energy so as to instantaneously change the frequency of said transmitter coil current;
   wherein the transition time between said distinct states is approximately zero.

2. A method for frequency-shift-keyed modulation of a transmitter coil current of a high-Q resonant circuit transmitter as in claim 1 wherein the operation of said high-Q resonant circuit transmitter during said distinct states is independent between said states.

3. A method for frequency-shift-keyed modulation of a transmitter coil current of a high-Q resonant circuit transmitter as in claim 1, wherein said distinct states are characterized by a high and low frequency.

4. A method for frequency-shift-keyed modulation of a transmitter coil current of a high-Q resonant circuit transmitter as in claim 1, wherein switching between said distinct states is accomplished with little to no energy loss.

5. In a frequency-shift-keyed demodulation receiver circuit, for decoding a frequency-shift-keyed signal having multiple half cycles, the improvement comprising:
   a means for decoding said frequency-shift-keyed signal by comparing the time duration of one or more of said half-cycles of said frequency-shift-keyed signal to an average value of the time duration of multiple half-cycles of said frequency-shift-keyed signal;
   wherein said means for decoding comprises a multiphase demodulator;
   and wherein said multiphase demodulator comprises one or more averaging capacitors and one or more threshold detectors.

6. A method for frequency-shift-keyed demodulation of an alternating current waveform having multiple half-cycles, comprising:
   comparing the time duration of one or more half-cycles of said alternating current waveform to an average value of the time duration of multiple half-cycles of said alternating current waveform;
   accomplishing said comparison of the average of multiple time durations by using one or more averaging capacitors.

7. A power and communication system for an inductively coupled device comprising:
   a high-Q resonant circuit transmitter;
   a means for producing frequency-shift-keyed modulation of a transmitter coil current whereby the frequency of said transmitter coil current is substantially instantaneously changed in a manner that results in little to no energy loss from the transmitter circuit; and
   a frequency-shift-keyed demodulation circuit whereby said demodulation circuit comprises means for decoding a frequency-shift-keyed signal by comparing the time duration of one or more half-cycles of said frequency-shift-keyed signal to an average value of the time duration of multiple half-cycles of said frequency-shift-keyed signal;
   wherein said frequency-shift-keyed demodulation circuit comprises a multiphase demodulator;
   and wherein said multiphase demodulator comprises one or more averaging capacitors and one or more adaptive threshold detectors.

* * * * *